United States Patent
Rabion et al.

(10) Patent No.: US 7,179,368 B2
(45) Date of Patent: Feb. 20, 2007

(54) METHOD FOR DESULFURIZING THIOPHENE DERIVATIVES CONTAINED IN FUELS

(75) Inventors: Alain Rabion, Pau (FR); Francois Fajula, Teyran (FR); Jean René Bernard, Serezin Du Rhone (FR); Vasile Hulea, Iasi~ (RO)

(73) Assignee: ELF Antar France, Courbevoie (FR)

( * ) Notice: Subject to any disclaimer, the term of this patent is extended or adjusted under 35 U.S.C. 154(b) by 145 days.

(21) Appl. No.: 10/169,030

(22) PCT Filed: Dec. 28, 2000

(86) PCT No.: PCT/FR00/03711

§ 371 (c)(1),
(2), (4) Date: Nov. 18, 2002

(87) PCT Pub. No.: WO01/48119

PCT Pub. Date: Jul. 5, 2001

(65) Prior Publication Data

US 2003/0102252 A1    Jun. 5, 2003

(30) Foreign Application Priority Data

Dec. 28, 1999   (FR) ................................ 99 16559

(51) Int. Cl.
*C10G 17/02*     (2006.01)
*C10G 27/04*     (2006.01)
*C10G 17/00*     (2006.01)

(52) U.S. Cl. .................. 208/219; 208/196; 208/208 R; 208/226; 208/240

(58) Field of Classification Search ................ 208/196, 208/208 R, 219, 226, 240
See application file for complete search history.

(56) References Cited

U.S. PATENT DOCUMENTS 3,039,855 A * 6/1962 Urban ...................... 423/573.1

(Continued)

FOREIGN PATENT DOCUMENTS

EP           29472 A1 *  6/1981

(Continued)

OTHER PUBLICATIONS

SU1203102A abstract 01-1985.*

(Continued)

*Primary Examiner*—Glenn Caldarola
*Assistant Examiner*—John Douglas
(74) *Attorney, Agent, or Firm*—Sughrue Mion, PLLC

(57) ABSTRACT

The invention concerns a method for selectively desulphurizing thiopene compounds contained in hydrocarbons derived from crude oil distillation, whether refined or not, which consists in oxidising the thiophene sulphur atoms into sulphone in the presence of an oxidising agent and in separating said sulphonated compounds from said hydrocarbons. The invention is characterised in that it consists in oxidising the thiophene compounds in a two-phase turbulent medium comprising a hydrocarbon phase and an aqueous phase, in the presence of at least an oxidising agent soluble in at least one of the two phases and of at least a metal catalyst in soluble or dispersed form in a liquid of in solid form, separation and oxidation occurring simultaneously.

23 Claims, 1 Drawing Sheet

U.S. PATENT DOCUMENTS

Figure 1:
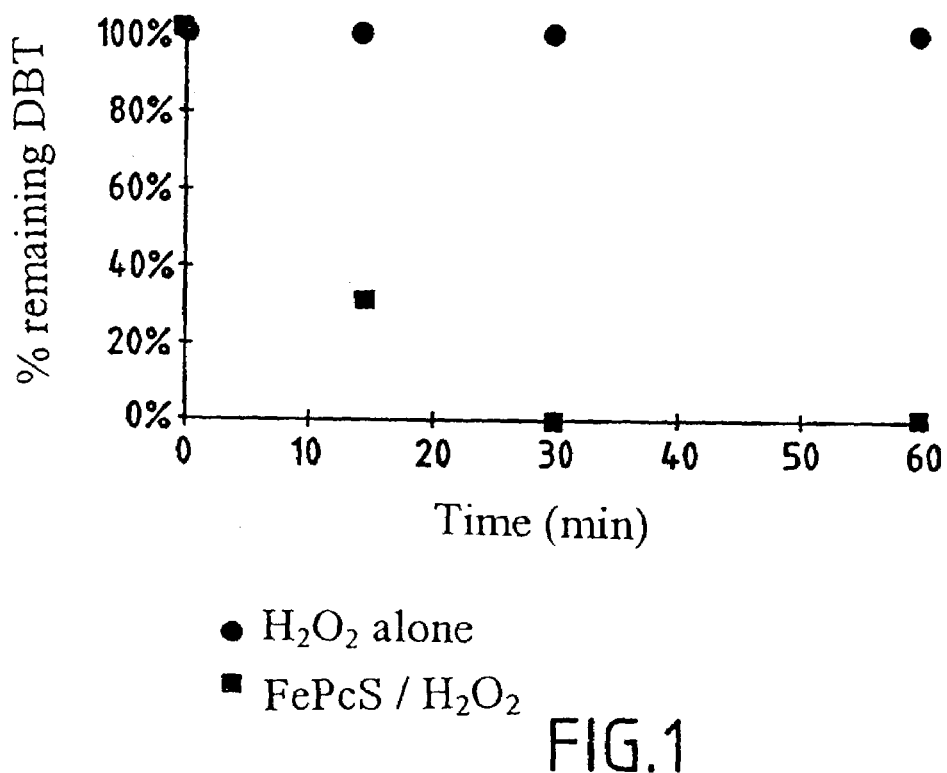

| | | | | |
|---|---|---|---|---|
| 3,445,380 A | * | 5/1969 | Urban | 208/206 |
| 3,551,328 A | * | 12/1970 | Cole et al. | 208/240 |
| 3,647,683 A | * | 3/1972 | Kelly | 208/196 |
| 3,816,301 A | * | 6/1974 | Sorgenti | 208/208 R |
| 6,171,478 B1 | * | 1/2001 | Cabrera et al. | 208/212 |
| 6,368,495 B1 | * | 4/2002 | Kocal et al. | 208/240 |

FOREIGN PATENT DOCUMENTS

| | | | |
|---|---|---|---|
| EP | 115382 A1 | * | 8/1984 |
| EP | 565324 A1 | * | 10/1993 |
| FR | 1595726 A | * | 6/1970 |

OTHER PUBLICATIONS

SU1549985A abstract 03-1990.*

* cited by examiner

- H₂O₂ alone
- FePcS / H₂O₂

METHOD FOR DESULFURIZING THIOPHENE DERIVATIVES CONTAINED IN FUELS

This invention relates to a method for desulfurizing fuels, namely gas oils, kerosenes and gasolines. In particular, it targets the desulfurization of fuels that contain thiophene compounds.

The presence of sulfur in fuels is a problem considered today as a major problem for the environment. Indeed, the sulfur is converted, through combustion, into various sulfur oxides, that can transform into acids, thus contributing to the formation of acid rains.

In general, refineries use catalytic hydrodesulfurizing methods to lower the sulfur content of fuels. Thus, the gas oils that are derived directly from the distillation are treated in reactors that operate at temperatures ranging between 300 and 400° C., a hydrogen pressure that ranges between 30 and $100.10^5$ Pa (between 30 and 100 bars) and hourly space velocities that range between 0.5 and 4 $h^{-1}$. The fuel's sulfur compounds react with the hydrogen when in contact with the catalyst arranged in a fixed bed and comprised of metal sulfides from groups VI and VIII supported on alumina, for example cobalt and molybdenum sulfides or nickel and molybdenum sulfides. Because of the operational conditions and the consumption of hydrogen, these methods can be costly both in investments and in operation, and more so in cases where we seek to produce fuels with a very low sulfur content. Thus, to desulfurize a fuel that initially contains 1% by weight of sulfur to a sulfur content that ranges between 0.05 and 0.005% by weight, the size of the reactor can be multiplied by 4 and we must also increase the quantity of hydrogen necessary for the reaction. We thus understand why it is particularly difficult to eliminate traces of sulfur, in particular if the sulfur is contained in refractory molecules such as dibenzothiophene with alkyl substituents in position 4, or 4 and 6.

In some countries, such as Sweden, the United States (in particular in California) and others, the total sulfur content of gas oils is already limited to 0.005% by weight. This limitation could eventually become the standard in the countries belonging to the OECD.

At the same time, in France, the total sulfur content in gasolines is limited to 0.05% by weight, but this limit could soon be lowered to 0.005% by weight or less in 2005 and this for all of Europe.

Gasolines, as opposed to gas oils, are not only obtained through direct distillation, but also through various methods such as naphtha reforming, light naphtha isomerization, the alkylation of butane or propane that produce iso-octane, isobutene methoxylation and catalytic cracking of vacuum distillates or of atmospheric residues. Cracking generates between 20 and 60% by weight of the final gasoline and it is the gasolines that are produced using this method that bring the sulfur compounds into the gasoline, except for the low quantities of sulfur present in the direct distillation gasolines.

To desulfurize these cracked gasolines, usually methods similar to those described for the hydrodesulfurization of gas oils are used, where the operational conditions for hydrogen pressure, space velocity and temperature are stricter. Again, these methods are costly in investments, in operation and in hydrogen, because of the sulfur contents we want to reach. It is however possible, using traditional manners, to reach total sulfur contents in said cracked gasolines that range between 0.005 and 0.03% by weight, based on the quantity of treated hydrocarbons and the severity of the hydrotreating of said hydrocarbons prior to the cracking step. In the absence of hydrotreatment, the total sulfur content in the cracked gasoline could reach up to 0.1% by weight. To reduce this sulfur content, additives that decompose the thiols and sulfurs that are formed in the gasoline that is gathered can be added to the cracking catalyst. Unfortunately, these additives have little or no effect on the benzothiophene derivatives, even if hydrocarbons charged in the catalytic cracking unit were previously hydrodesulfurized, meaning that the thiols and sulfurs have been removed.

One major disadvantage of the hydrodesulfurizing of cracked gasolines is that, along with the desulfurizing, there is a partial hydrogenation of the olefins. Yet, said olefins are responsible for the good gasoline octane number, and their disappearance results in a reduction of this number, thus a lesser quality gasoline. To compensate for this loss, either other constituents that will improve this number can be introduced, or the gasoline itself can be re-treated so as to increase this number. As adding a new treatment or new compounds to the gasoline in order to improve the quality is also a burden on its cost price, we understand the advantage of a treatment method for desulfurizing the sulfur compounds, and more selectively, the benzothiophene compounds, that leaves the non sulfurized molecules intact and limits the use of hydrogen.

The methods using selective oxidation of sulfur compounds can fulfill this role. From the methods and procedures developed to reduce the quantity of sulfur present in fuels in the form of thiophene derivatives, oxidation by organic peroxides, organic hydroperoxides, hydrogen peroxide and organic peracids in the presence or in the absence of catalysts based on organometallic compounds or metallic oxide, has been considered (see U.S. Pat. No. 3,668,117, U.S. Pat. No. 3,565,793, EP 0 565 324 and publications by T. A. KOCH, K. R. KRAUSE, L. EMANZER, H. MEHDIZADEH, J. M. ODOM, S. K. SENGUPTA, New J. Chem., 1996, 20, 163–173 and by F. M. COLLINS, A. R. LUCY, C. SHARP, J of Molecular Catalysis A: Chemical 117 (1997) 397–403).

For the methods that use molybdenum and tungsten based metal catalysts in the presence of hydrogen peroxide, operation temperatures are greater than 60° C. and there is an over consumption of hydrogen peroxide, a portion of this oxidizing agent being decomposed by the catalyst being used. The use of peracids, very strong oxidizing agents obtained by reaction of hydrogen peroxide with a carboxylic acid such as formic acid or acetic acid, is very dangerous at these temperatures in hydrocarbon environments, because of the risk of explosion in the case of a shock or in the presence of light. Furthermore, they are less efficient than hydrogen peroxide and less selective towards the sulfur compounds, so that they can oxidize olefins.

In all these methods and procedures, thiophene derivatives are transformed into their sulfonated and/or sulfonic form. However, for some of these compounds, reaction even at high temperatures, is relatively slow and the total conversion is not reached in less than one hour, unless very strong concentrations of oxidizing agents are used, often much higher than the quantities necessary for a quasi-stoichiometric oxidation of the sulfur derivatives.

Other methods of oxidation use phthalocyanines or metal polyphthalocyanines in the presence of oxygen or ozone to transform the thiols and the $H_2S$ contained in the oil products into organic disulfides, as described, for example, in the U.S. Pat. Nos. 3,565,959 and 3,039,855. However, such methods do not allow for the oxidization of the thiophene compounds that remain in the oil products. Furthermore, when applied to catalytic cracked gasolines, these methods favor the formation of fuel gums through the polymerization of the olefins, which makes the gasolines improper for use.

Therefore, the objective of this invention is to propose a method for desulfurizing fuels that contain thiophene compounds without reducing the octane number or the cetane number, sometimes even increasing them. In particular it relates to the finishing treatment of hydrotreated gas oils, kerosenes and catalytic cracking gasolines, with high concentrations of thiophene compounds resistant to hydrogenations.

Therefore, the subject matter of this invention is a method for selectively desulfurizing the thiophene compounds contained in the refined or unrefined hydrocarbons derived from the crude oil distillation, comprising oxidizing the thiophene sulfur atoms into sulfone in the presence of an oxidizing agent, and separating said sulfone compounds from said hydrocarbons, characterized in that the thiophene compounds are oxidized in a two-phase turbulent medium comprising a hydrocarbon phase and an aqueous phase, in the presence of at least an oxidizing agent soluble in at least one of the two phases and of at least one metal catalyst chosen from the metallic phtalocyanines, possibly substituted with alkyl groups comprising 1 to 4 carbon atoms and/or sulfonic groups, and the catalysts comprising a support selected from the group consisting of the silicas, aluminas, zirconias, amorphous or crystalline aluminosilicates, aluminophosphates and mesoporous solids, alone or mixed with each other, possibly comprising at least one metal selected from the group consisting of titanium, zirconium, vanadium, chromium, molybdenum, iron, manganese, and tungsten, where said metals can be introduced into the network of the support or impregnated in complex form or non-complex form. Among said catalysts, the non oxidized titanium catalysts are preferred.

The method as set forth in the invention has the advantage of allowing for a selective oxidation of the thiophene sulfur into sulfone. The separation of the sulfones from the hydrocarbons is immediate, the latter passing into the aqueous phase. Furthermore, this oxidation has no effect on the olefins, the octane number or the non-sulfurized aromatic compound content of the catalytic cracking gasoline thus remaining unchanged. Furthermore, the oxidation method as set forth in the invention improves the cetane number of the gas oils.

These specific effects are linked to the synergy effect of the selected oxidizing agents and the catalysts used.

Thus, in the context of this invention, the oxidizing agent is chosen from the group consisting of organic peroxides, hydrogen peroxide, organic hydroperoxides, peracids and alkaline and alkaline-earth persulfates.

To complete the extraction, meaning the passing of the sulfonated thiophene compounds from the hydrocarbon phase to the aqueous phase and accelerate the oxidation reaction, to the two-phase reaction medium, a solvent miscible with water and hardly miscible with hydrocarbons, chosen from the group consisting of alkanols that contain from 1 to 4 carbon atoms, acetonitrile, dimethyl formamide, nitromethane, nitrobenzene, is added to the two-phase reaction medium in a water/solvent ratio ranging between 1/99 and 99/1 and preferably between 25/75 and 75/25. To recuperate the sulfonated compounds derived from the oxidation reaction, one could also proceed using distillation and/or absorption on a refractory oxide of the alumina or silica type, and/or precipitation of said oxidized compounds, based on known procedures, such as described in the European patents 0 585 324 and 0 482 841.

In a preferred embodiment of the method set forth in the invention, the metal catalyst (expressed in metal)/oxidizing agent molar ratio varies between $1/10^5$ and 100/1 in the two-phase reaction medium, the reaction temperature ranges between the ambient temperature and 90° C., and preferably between 50 and 90° C., under atmospheric pressure, and the aqueous solution's pH it maintained below 12 and preferably between 4 and 9.

In a particular embodiment of the invention, from the metal catalysts consisting of metal phthalocyanines, the iron phthalocyanines, possibly substituted with alkyl groups comprised of 1 to 4 carbon atoms and/or sulfone groups, in an aqueous solution or supported on a solid phase chosen from the refractory metal oxides group such as alumina, zirconia, silica, tungstate, clays and organic resins such as cationic resins functionalized with ammonium groups are preferred. In this embodiment, the metal phthalocyanines are not substituted with sulfonic groups and can be linked to the support by ionic or covalent links of the sulfonamide type.

When the metal catalyst is a non oxidized titanium catalyst, titanium zeolites, without extra-network titanium, with a pore diameter of at least 0.65 nm, and titanium mesoporous composites, and more particularly titanium beta zeolite are preferred. Said zeolites can be prepared by implementing the method described in the European patent 0 842 114.

In this particular embodiment of the invention, the metal catalyst (expressed in metal) oxidizing agent molar ratio varies from 1/10 to 1/40 in the two-phase reaction medium.

According to the invention, the oxidizing agents are chosen from the compounds with a general formula of $R_1OOR_2$, where $R_1$ and $R_2$ are identical or different, chosen from hydrogen and linear or branched alkyl groups, comprised of 1 to 30 carbon atoms.

In a preferred embodiment, the oxidizing agent whose formula is $R_1OOR_2$ is chosen from the group consisting of hydrogen peroxide, terbutyl hydroperoxide and terbutylperoxide. The preferred oxidizing agents are terbutylperoxide and hydrogen peroxide, where the latter is greatly preferred because of its low pollution effect.

Other oxidizing agents of the invention, i.e. peracids of formula $R_3COOOH_2$ are chosen so that $R_3$ is hydrogen or a linear or branched alkyl group consisting of 1 to 30 carbon atoms. They are preferably chosen from the group consisting of peracetic acid, performic acid and perbenzoic acid. To avoid any problems with explosions, they are formed in situ by progressively adding a small quantity of a hydrogen peroxide/carboxylic acid mix.

No matter which oxidizing agent and catalyst are used, the aqueous solution/hydrocarbons mass ratio varies from 10/1 to 1/1. Preferably we will operate with a ratio that varies from 2/1 to 1/5.

A second subject matter of the invention is the application of the method as defined above to the specific finishing treatment of the gasolines derived from catalytic cracking or to the treatment of gas oils that have been previously hydrotreated and kerosenes, so the method is more economical.

The object of the examples hereafter is to illustrate the efficiency of the method as set forth in the invention, without limiting its scope.

In these examples, we will refer to FIGS. 1 and 2 of the attached drawings, that will be explained in Examples I and V respectively.

EXAMPLE I

The object of this example is to show the activity of the metal phthalocyanine/hydrogen peroxide combination with regard to the oxidation of the thiophene derivatives present in fuels, mainly benzothiophene (BT), dibenzothiophene (DBT) and dimethyldibenzothiophene 4.6 (DMBT).

The metal phthalocyanines used are iron sulfophthalocyanines (FePcS), cobalt sulfophthalocyanines (CoPcS) and nickel sulfophthalocyanines (NiPcS). Test were carried out in an organo (acetonitrile/water)aqueous two phase medium with a pH of 7.7, where the oxidizing agent metal phthalocyanine ratio is 20/1, the temperature is the ambient temperature of 20° C. and the pressure is the atmospheric pressure and the mixture is agitated.

As comparison tests and to show the efficacy of the catalyst, oxidation of the same thiophene derivates is carried out, on the one hand, in the presence of a catalyst comprised of a zeolite TS-1 (zeolites whose pore diameter is less than 0.6 nm) and hydrogen peroxide $H_2O_2$ and, on the other hand, in the presence of iron phthalocyanine and atmospheric oxygen.

The thiophene derivatives to be oxidized are introduced into the acetonitrile at 1 mmole/l. Table 1 hereafter shows the results in percentage of oxidation obtained after 30 minutes of reaction.

TABLE 1

| Catalyst / Oxidizing Agent | Oxidizing Agent Concentration (eqS) | % sulfone oxidation | | |
|---|---|---|---|---|
| | | BR (1 mM) | DBT (1 mM) | DMBT(1 mM) |
| $H_2O_2$ | 2 | 3 | <1 | <1 |
| FePcS (air) | | 0 | 0 | 0 |
| FePcS/$H_2O_2$ | 2 | 90 | 95 | 95 |
| FePcS/$H_2O_2$ | 3 | 100 | 100 | 100 |
| CoPcS/$H_2O_2$ | 2 | <1 | <1 | <1 |
| NiPcS/$H_2O_2$ | 2 | <1 | <1 | <1 |
| TS-1/$H_2O_2$ | 2 | 0 | 0 | 0 |

FIG. 1 is a curve that illustrates the evolution of the DBT (dibenzothiophene) content remaining in the acetonitrile/water two-phase medium based on time.

At room temperature and atmospheric pressure, the oxidation of the thiophene derivatives by the peroxides alone or by the sulfonated metal phthalocyanine alone in an aerated medium is ineffective.

However, the iron phthalocyanines/peroxide couples catalyze the oxidation of the thiophene BT, DBT and DMBT derivatives into sulfone very effectively. Note that the DMBT, a substrate that is difficult to oxidize because of the steric hindrance of the methyl groups in position β of sulfur is oxidized as quickly as the DBT.

On the contrary, the cobalt and nickel sulfophthalocyanines, as well as the TS-1 are inefficient for such an oxidation under the conditions of the reaction.

EXAMPLE II

The object of this example is to present the oxidation of the dibenzothiophene in a liquid/liquid two-phase catalyst system, by choosing heptane as the solvent for the organic phase. The aqueous phase consists of pH7.7 buffer consisting of phosphate and acetone, so as to solubilize the iron sulfophthalocyanine and a minimum of DBT (initial partition of the DBT 95:5, organic phase/aqueous phase).

We operate under the following conditions:

DBT: 1 mmol/l; FePcS 0.1 mmol/l; $H_2O_2$: added continuously 5 eq/h; temperature: 20° C.; atmospheric pressure; magnetic agitation.

Under the reaction conditions being used, the catalyzed oxidation of DBT is complete after 30 minutes of reaction, i.e. after adding 2.5 equivalents of $H_2O_2$. The DBT is entirely converted into the corresponding sulfone that is stable with regard to the oxidizing system used and partitions between the two phases (final ratio of the sulfone 1/3, organic phase/aqueous phase).

EXAMPLE III

This example relates to oxidation in a three-phase mixture, when the catalyst is a non oxidized titanium catalyst in a solid dispersed form in the two-phase reaction mixture. Two types of catalyst were tested: Ti-beta (zeolite with a BEA structure) and Ti-HMS (titanium mesoporous composite). The Ti-beta (without extra-network titanium) was obtained from a post-treated commercial zeolite as set forth in the procedure described in the European patent 0 842 114.

The titanium mesoporous composite was obtained by co-precipitation, in a highly acid medium, of silicate and titanium oxide, in the presence of a pluronic type non ionic surfactant.

The catalyst' main characteristics are presented in Table 2 hereafter.

TABLE 2

| Catalyst | Ti/(Ti + Si) mole/mole | BET surface $m^2$/g | Diameter of particles, μ | Vmp (ml/g) |
|---|---|---|---|---|
| Ti-beta | 0.008 | 470 | 0.3 | 0.28 |
| Ti-HMS | 0.024 | 838 | 10 | 0.42 |

The oxidizing agent used is hydrogen peroxide. The fraction to be oxidized is a benzothiophene and dibenzothiophene solution in n-decane. The reaction medium containing 0.5 mmole of benzothiophene, 0.5 mmole of dibenzothiophene, 20 ml of n-decane, 1 ml of aqueous solution containing 30% by weight of hydrogen peroxide, 100 mg of catalyst and 20 ml of a solvent non miscible in n-decane that can be an alcohol, acetonitrile or water are introduced into a 60 ml reactor. The medium is vigorously agitated using a magnetic agitator and is maintained at a temperature of 70° C. (or 64.5° C. if methanol is the solvent) at atmospheric pressure.

After the reaction, the hydrocarbon and aqueous phases are separated by simple decantation.

The conversions of the sulfur compounds are presented in Table 3 below, after five hours of reaction.

TABLE 3

| Catalyst | Solvent | Conversion % | |
|---|---|---|---|
| | | Benzothiophene | Dibenzothiophene |
| Ti-HMS | Acetonitrile | 56.0 | 67.0 |
| Ti-beta | Methanol | 100 | 93.7 |
| Ti-beta | Acetonitrile | 96.7 | 91.0 |
| Ti-beta | Water | 64.3 | 25.0 |

We notice from these results that both catalysts are efficient in oxidizing thiophenes. The efficiency of the solvent is linked to the solubility of the oxidation products. Thus, they are much more soluble in methanol and acetonitrile than in water.

EXAMPLE IV

The object of this example is oxidation in a three-phase mixture when the catalyst is not a titanium catalyst. We operate as described in Example III.

Among the catalysts used in this example, the HMS mesoporous solid based catalysts are obtained by co-precipitation in a highly acidic medium, of silicate and vanadium, tungsten, or molybdenum oxide, in the presence of a non ionic surfactant of the pluronic type.

The alumina or zirconia based catalysts are obtained by impregnation by wet process of ammonium metatungstate or vanadate in an aqueous solution, followed by drying and lastly calcination at 500° C.

Table 4 hereafter presents the results obtained with these catalysts.

TABLE 4

| | | Conversion, % | |
|---|---|---|---|
| Catalyst | Solvent | Benzothiophene | Dibenzothiophene |
| V-HMS | Methanol | 40.0 | 45.0 |
| V-HMS | Acetonitrile | 51 | 55 |
| Mo-HMS | Acetonitrile | 32 | 36 |
| W-HMS | Acetonitrile | 20 | 27 |

It is obvious, from this table and the previous example, that the efficiency of the desulfurizing of the dibenzothiophene derivatives depends greatly on the compromise, the nature of the support, the nature of the metal and the nature of the extraction solvent of the sulfones that are formed. Under the operational conditions of Example III, titanium catalysts seem to be the most efficient.

EXAMPLE V

The object of this example it to describe the oxidation kinetic of sulfur compounds contained in kerosene. The catalyst being used is Ti-beta, whose characteristics are presented in Example III. The fraction being treated is a kerosene that contains 1310 ppm of sulfur, present in most sulfur compounds in the form of thiophene compounds.

The reaction medium containing 40 ml of kerosene, 0.35 ml of aqueous solution at 30% by weight of hydrogen peroxide, 1 g of catalyst and 20 ml of acetonitrile is introduced into a 100 ml reactor. The medium is vigorously agitated using a magnetic agitator and is maintained at a temperature of 60° C., at atmospheric pressure. The kerosene is then washed using acetonitrile to finish the separation before measuring the total sulfur content.

Figure 2:
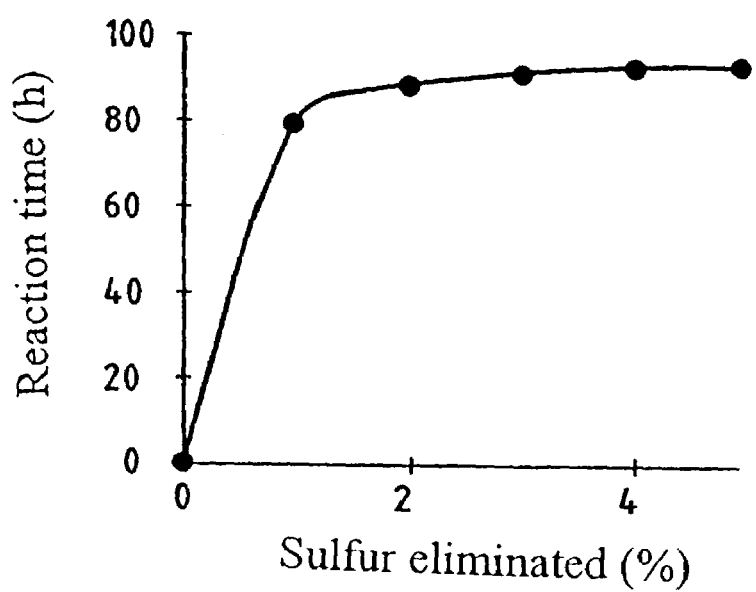

The kerosene desulfurization rate based on the reaction time is presented in FIG. 2.

We note from this figure that after 2 hours, 90% of the sulfur is eliminated. The oxidized sulfur compounds pass fully in the phase that contains the acetonitrile and water.

EXAMPLE VI

The object of this example is oxidation in a three-phase mixture when the catalyst is a non oxidized titanium catalyst in its dispersed solid form in the two-phase reaction mixture. Two types of catalyst were tested: Ti-beta and Ti-HMS, whose characteristics are presented in Example III.

The fraction being treated is kerosene that contains 1310 ppm of sulfur, for the most part in the form of thiophene compounds.

The reaction medium consisting of 40 ml of hydrocarbons, 2 ml of aqueous solution (30% gr) of hydrogen peroxide, 200 mg of catalyst and 20 ml of a solvent that is not miscible with hydrocarbons, that may be an alcohol, acetonitrile or water is introduced into a 100 ml reactor. The medium is vigorously agitated using a magnetic agitator and is maintained at a temperature of 70° C., at atmospheric pressure.

After the reaction, the three phases (kerosene, solvent+ water, catalyst) were separated by filtration and decantation. No other operation was carried out on the fractions before they were analyzed.

The efficiency of the catalysts taken in the presence of hydrogen peroxide is measured by the decrease of sulfur in the supernatant hydrocarbonated phase. The results are provided in Table 5 hereafter.

TABLE 5

| Catalyst | Solvent | Reaction time (h) | Phase being analyzed | Sulfur, ppm | % sulfur eliminated |
|---|---|---|---|---|---|
| | Acetonitrile | Extraction | Kerosene | 1220 | 7.0 |
| Ti-HMS | Acetonitrile | 9 | Kerosene | 190 | 85.5 |
| | | 9 | MeCN | 2500 | |
| Ti-beta | Acetonitrile | 5 | Kerosene | 80 | 94.0 |
| | | 5 | MeCN | 2300 | |
| Ti-beta | Ethanol | 5 | Kerosene | 390 | 70.2 |
| | | 10 | | 300 | 77.00 |
| | | 24 | | 250 | 81.0 |
| | | 24 | Kerosene washed in acetonitrile | 80 | 94.0 |
| | | 24 | EtOH | 1800 | |
| Ti-beta | H$_2$O | 10 | Kerosene | 840 | 86.0 |
| | | 10 | Kerosene washed in acetonitrile | 300 | 77.1 |
| | | 10 | H$_2$O | 450 | |

We note, from this table, that both catalysts are just as efficient in oxidizing the sulfur in the present kerosene. The oxidation products (sulfones) are not very soluable in hydrocarbons and they pass into the solvent. The efficiency of the solvent is linked to the solubility of the sulfones: acetonitrile>ethanol>water.

The invention claimed is:

1. Method of selective desulfurizing of thiophene compounds contained in refined or unrefined hydrocarbons derived from the distillation of crude oil, comprising:
   oxidizing thiophene sulfur atoms into sulfone in the presence of an oxidizing agent; and
   separating the sulfone compounds from said hydrocarbons,
   characterized in that the thiophene compounds are oxidized in a two-phase turbulent phase consisting of a hydrocarbon phase and an aqueous phase, in the presence of at least one oxidizing agent soluble in at least one of the two phases, the oxidizing agent being selected from the group consisting of organic peroxides, hydrogen peroxide, organic hydroperoxides, peracids, alkaline persulfates, and alkaline earth persulfates, and in the presence of at least one metal catalyst selected from the group consisting of (1) metal phthalocyanines and (2) catalysts comprising (i) a support selected from the group consisting of silicas, aluminas, zirconias, amorphous or crystalline aluminosilicates, aluminophosphates, mesoporous solids, and mixtures thereof, and (ii) at least one metal selected from the group consisting of titanium, zirconium, vanadium, chromium, molybdenum, iron, manganese and tungsten, where said metal (ii) can be introduced into the support network or impregnated in complex or non complex form, wherein the separation and the oxidation occur simultaneously, and wherein the aqueous solution pH is kept under 12.

2. Method as set forth in claim 1, characterized in that an extraction solvent selected from the group consisting of alcanols comprised of 1 to 4 carbon atoms, acetonitrile, formamide dimethyl, nitromethane, and nitrobenzene is added to the two-phase reaction medium, in a water/solvent ratio ranging between 1/99 and 99/1.

3. Method as set forth in claim 1, characterized in that the metal catalyst (expressed in metal)/oxidizing agent molar ratio ranges between $1/10^5$ and 100/1, and in that the reaction starts at ambient temperature and atmospheric pressure.

4. Method as set forth in claim 1, characterized in that the metal phthalocyanine is an iron phthalocyanine.

5. Method as set forth in claim 1, characterized in that the metal phthalocyanine is an iron phthalocyanine supported over a solid phase selected from the group consisting of refractory metal oxides, clays and organic resins.

6. Method as set forth in claim 1, characterized in that the oxidizing agent is a compound with a general formula of $R_1OOR_2$, where $R_1$ and $R_2$ are independently selected from the group consisting of hydrogen and linear or branched alky groups having 1 to 30 carbon atoms.

7. Method as set forth in claim 6, characterized in that the oxidizing agent is selected from the group consisting of hydrogen peroxide, terbutyl hydroperoxide and terbutyl peroxide.

8. Method as set forth in claim 6, characterized in that the oxidizing agent is hydrogen peroxide.

9. Method as set forth in claim 1, characterized in that the oxidizing agent is a peracid with a formula of $R_3COOOH$, where $R_3$ is hydrogen or a linear or branched alkyl group comprised of 1 to 30 carbon atoms.

10. Method as set forth in claim 9, characterized in that the oxidizing agent is selected from the group consisting of peracetic acid, performic acid and perbenzoic acid.

11. Method as set forth in claim 1, characterized in that the aqueous solution/hydrocarbon mass ratio ranges between 10/1 and 1/10.

12. Method as set forth in claim 1, wherein the hydrocarbons are selected from the group consisting of hydrotreated gas oils, kerosenes and gasolines.

13. Method as set forth in claim 1, wherein the metal phthalocyanines are substituted by alkyl groups consisting of 1 to 4 carbon atoms and/or sulfonic groups.

14. Method as set forth in claim 2, wherein the water/solvent ratio ranges between 25/75 and 75/25.

15. Method as set forth in claim 3, wherein the aqueous solution pH ranges between 4 and 9.

16. Method as set forth in claim 4, wherein the iron phthalocyanine is substituted by alkyl groups comprised of 1 to 4 carbon atoms and/or sulfonic groups in an aqueous solution.

17. Method as set forth in claim 5, wherein the iron phthalocyanine is substituted by alkyl groups comprised of 1 to 4 carbon atoms and/or sulfonic groups, the refractory metal oxides are selected from the group consisting of alumina, zirconia, silica, and tungstate, and the organic resins are cationic resins functionalized by ammonium groups.

18. Method as set forth in claim 11, wherein the aqueous solution/hydrocarbon mass ratio ranges between 2/1 and 1/5.

19. Method as set forth in claim 12, wherein the gasolines are gasolines derived from catalytic cracking.

20. Method of selective desulfurizing of thiophene compounds contained in refined or unrefined hydrocarbons derived from the distillation of crude oil, comprising:

oxidizing thiophene sulfur atoms into sulfone in the presence of an oxidizing agent; and separating the sulfone compounds from said hydrocarbons, characterized in that the thiophene compounds are oxidized in a two-phase turbulent phase consisting of a hydrocarbon phase and an aqueous phase, in the presence of at least one oxidizing agent soluble in at least one of the two phases, the oxidizing agent being selected from the group consisting of organic peroxides, hydrogen peroxide, organic hydroperoxides, peracids, alkaline persulfates, and alkaline earth persulfates, and in the presence of at least one metal catalyst selected from the group consisting of (1) metal phthalocyanines and (2) catalysts comprising (i) a support selected from the group consisting of silicas, aluminas, zirconias, amorphous or crystalline aluminosilicates, aluminophosphates, mesoporous solids, and mixtures thereof, and (ii) at least one metal selected from the group consisting of titanium, zirconium, vanadium, chromium, molybdenum, iron, manganese and tungsten, where said metal (ii) can be introduced into the support network or impregnated in complex or non complex form, characterized in that the metal catalyst is a titanium catalyst selected from the group consisting of titanium zeolite without extra-network titanium, with a pore diameter greater than or equal to 0.65 nm and titanium mesoporous composites, and wherein the separation and the oxidation occur simultaneously.

21. Method as set forth in claim 20, characterized in that the metal catalyst (expressed in metal)/oxidizing agent molar ratio varies from 1/10 to 1/40.

22. Method as set forth in claim 20, wherein the titanium zeolite is titanium beta zeolite.

23. Method of selective desulfurizing of thiophene compounds contained in refined or unrefined hydrocarbons derived from the distillation of crude oil, comprising:

oxidizing thiophene sulfur atoms into sulfone in the presence of an oxidizing agent; and separating the sulfone compounds from said hydrocarbons, characterized in that the thiophene compounds are oxidized in a two-phase turbulent phase consisting of a hydrocarbon phase and an aqueous phase, in the presence of at least one oxidizing agent soluble in at least one of the two phases, the oxidizing agent being selected from the group consisting of organic peroxides, hydrogen peroxide, organic hydroperoxides, peracids, alkaline persulfates, and alkaline earth persulfates, and in the presence of at least one metal catalyst selected from the group consisting of (1) metal phthalocyanines and (2) catalysts comprising (i) a support selected from the group consisting of silicas, aluminas, zirconias, amorphous or crystalline aluminosilicates, aluminophosophates, mesoporous solids, and mixtures thereof, and (ii) at least one metal selected from the group consisting of titanium, zirconium, vanadium, chromium, molybdenum, iron, manganese and tungsten, where said metal (ii) can be introduced into the support network or impregnated in complex or non complex form, wherein the separation and the oxidation occur simultaneously, and wherein the metal catalyst is a non-oxidized titanium catalyst.

* * * * *